(12) United States Patent
Hasegawa (10) Patent No.: US 7,407,290 B2
(45) Date of Patent: Aug. 5, 2008

(54) METHOD OF INSPECTING MONOCULAR DIPLOPIA AND EYE MARK PATTERN FOR USE IN THE SAME

(76) Inventor: Masahiro Hasegawa, 602, Morisu Keionagayama, 16-3, Kaitori 1-chome, Tama-shi, Tokyo 206-0012 (JP)

( * ) Notice: Subject to any disclaimer, the term of this patent is extended or adjusted under 35 U.S.C. 154(b) by 323 days.

(21) Appl. No.: 11/337,343

(22) Filed: Jan. 23, 2006

(65) Prior Publication Data
US 2006/0227289 A1    Oct. 12, 2006

(30) Foreign Application Priority Data
Apr. 6, 2005    (JP)    ............................ 2005-109569

(51) Int. Cl.
*A61B 3/02*    (2006.01)
(52) U.S. Cl. ................... 351/239; 351/240; 351/241
(58) Field of Classification Search ......... 351/239–241, 351/246
See application file for complete search history.

(56) References Cited

U.S. PATENT DOCUMENTS 4,222,639 A * 9/1980 Sheedy ..................... 351/201
2002/0176051 A1* 11/2002 Saladin ..................... 351/239

* cited by examiner

*Primary Examiner*—Ricky L. Mack
*Assistant Examiner*—James R Greece
(74) *Attorney, Agent, or Firm*—Frishauf, Holtz, Goodman & Chick, P.C.

(57)    ABSTRACT

In order to examine a degree of monocular diplopia is easily examined in a quantitative manner, a plurality of circular eye marks are seen from a predetermined examination distance with a single eye of a patient to find a particular eye mark whose double vision images are observed to be circumscribed each other, and a degree of monocular diplopia is determined by a view angle of the relevant circular eye mark. Since the eye mark is formed as a circular pattern, a degree of monocular diplopia can be examined irrespective of an axial direction along which double vision images appear.

17 Claims, 6 Drawing Sheets

METHOD OF INSPECTING MONOCULAR DIPLOPIA AND EYE MARK PATTERN FOR USE IN THE SAME

BACKGROUND OF THE INVENTION

1. Field of the Invention

The present invention relates to a method of examining or checking a degree of monocular diplopia in a quantitative manner through a sight of a patient and an eye mark chart for use in such an examining method.

2. Related Art Statement

Monocular diplopia is a kind of double vision in which even when an object is viewed with a single eye, double vision images are observed. In the past, the monocular diplopia was scarcely observed, but recently the monocular diplopia due to generally caused deficient in refraction of optical system of an eye has been diagnosed frequently. A degree of double vision does not appear constantly, but has been found to change in a day. Monocular diplopia is caused by astigmatism accompanied by presbyopia, and thus highly aged people have frequently suffered from monocular diplopia. Therefore, it is preferable to provide a useful eye mark chart by means of which a patient can easily examine monocular diplopia in a quantitative manner.

There have been announced many studies about monocular diplopia and there have been proposed several methods of examining monocular diplopia by directly inspecting an optical system of an eye. However, any method has not been proposed to examine a degree of monocular diplopia quantitatively in an easy manner by utilizing sight of a patient.

SUMMERY OF THE INVENTION

The present invention has for its object to provide a method of examining a degree of monocular diplopia quantitatively in an easy manner by utilizing sight of a patient. It is another object of the invention to provide an eye mark chart by means of which a patient can examine a degree of monocular diplopia quantitatively in an easy manner through a use of sight of patient.

According to the invention, a method of examining a degree of monocular diplopia of a patient, wherein a plurality of circular eye marks having different diameters are seen by a single eye of the patient to find a particular circular eye mark whose double vision images are observed to be circumscribed each other, and a degree of monocular diplopia of the patient is examined on a basis of a view angle of said particular circular eye mark.

According to the invention, an eye mark chart for use in a method of examining a degree of monocular diplopia in a quantitative manner in which a plurality of circular eye marks having different diameters are observed with a single eye of a patient to find a particular circular eye mark whose diplopia vision images are observed to be circumscribed each other and a degree of monocular diplopia is determined as a view angle of the relevant particular eye mark, comprises an arrangement of a plurality of circular eye marks having different diameters, said circular eye marks forming a line in order of size.

According to the invention, when a patient sees circular eye marks having different diameters with a single eye from a given examination distance, double vision images, i.e. two circular images of a circular eye mark are observed to be separated from each other or circumscribed each other or partially overlapped with each other depending upon a diameter of the circular eye mark. Then, a degree of monocular diplopia can be determined on a basis of a view angle for a circular eye mark whose double vision images are observed to be circumscribed each other. In this manner, according to the invention, a degree of monocular diplopia can be easily examined in a quantitative manner by utilizing sight of a patient.

BRIEF DESCRIPTION OF THE DRAWINGS

FIGS. 1(*a*)—1(*d*) are diagrams explaining a principle of the monocular diplopia examining method according to the invention;

FIGS. 2(*a*)-2(*d*) are diagrams representing a geometrical relationship between an examination distance and diameters of circular eye marks;

DESCRIPTION OF THE PREFERRED EMBODIMENTS

Figure 1:
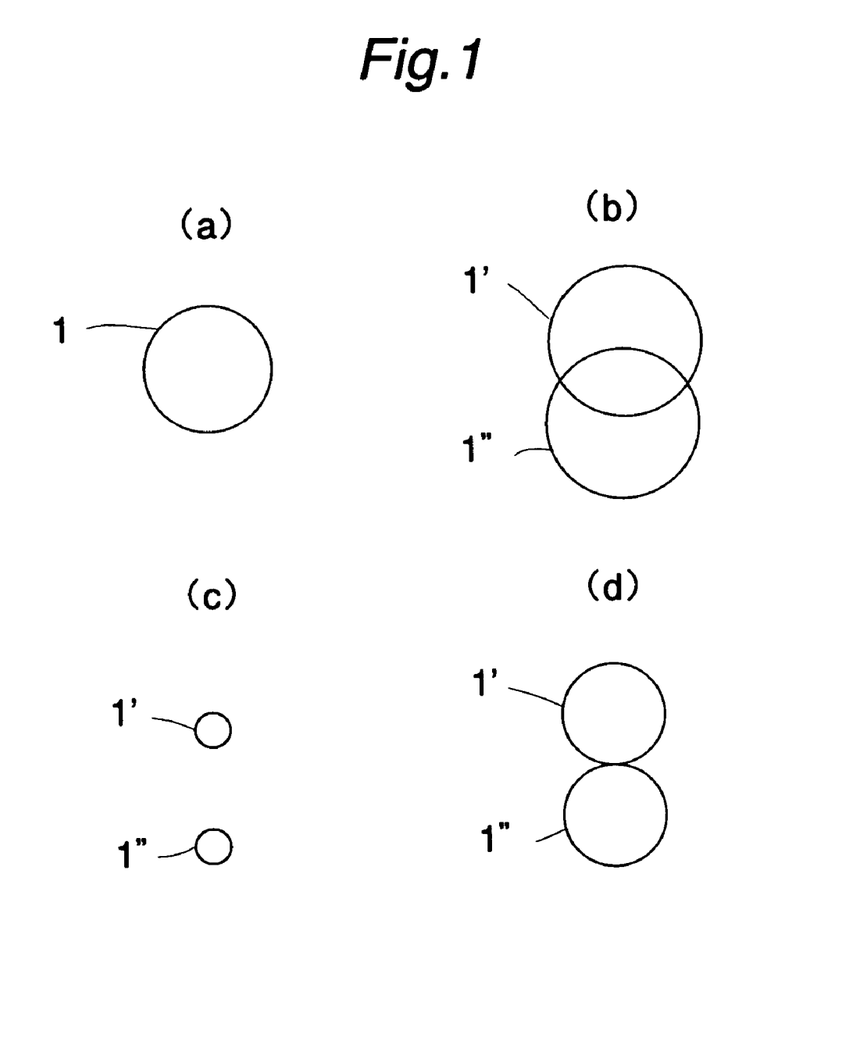

FIG. 1 is a diagram representing a principle of the monocular degree examining method according to the invention. FIG. 1(*a*) shows a circular eye mark 1 formed by a true circle. When a user or patient sees this circular eye mark with his or her single eye having monocular diplopia, double vision images, i.e. two images of circular eye mark are observed by the patient. Now it is assumed that the patient's eye under examination has monocular diplopia in an up and down direction. When the patient sees a circular eye mark having a larger diameter, double vision images 1' and 1" perceived by the patient are partially overlapped with each other in an up and down direction as illustrated in FIG. 1(*b*). When the patient sees a circular eye mark having a smaller diameter, double images 1' and 1" are observed separately from each other as depicted in FIG. 1(*c*). When a circular eye mark having an intermediate diameter is seen by the patient, double vision images 1' and 1" of the circular eye mark perceived by the user are circumscribed each other as shown in FIG. 1(*d*). That is to say, the double vision images 1' and 1' of the circular eye mark are just brought into contact with each other.

Now it is assumed that when a point is seen by a patient with a single eye having monocular diplopia from a predetermined examination distance, double vision images of the point are perceived by the patient as to be separated from each other by a distance R. Then, when a circular eye mark 1 having a diameter R is seen by the patient, two circular images 1' and 1" perceived by the patient are just circumscribed each other. If the circular eye mark has a diameter smaller than R, double vision images 1' and 1" are observed to be separated from each other as shown in FIG. 1(*c*), and if the circular eye mark has a diameter larger than R, double vision images 1' and 1" are perceived to be partially overlapped with each other as depicted in FIG. 1(*b*)

In FIG. 1, the circular eye mark 1 is formed by a circular line described on a white background, but according to the invention, the circular mark may be formed by a circular dot whose color or tone is different from that of a background. In this case, it is preferable to form the circular dot with light color. Then an overlapped portion of double vision images can be easily distinguished because this portion is seen with much deeper color.

In the examination method according to the invention, the circular eye marks 1 may be arranged at a point separated from a patient by a predetermined examination distance or may be displayed on a monitor screen of a suitable ophthalmology instrument. In the latter case, a plurality of circular eye marks having different diameters may be displayed successively or may be displayed simultaneously and a patient observes the circular eye marks through an eye lens formed by a convex lens.

When a user observes the circular eye marks with a naked eye, the eye marks has to be arranged at a position separated from a patient by a substantial distance. When the circular eye marks are displayed on a monitor screen of an ophthalmology instrument, the circular eye marks can be placed at a conjugate position to the patient's eye with respect to the eye lens, and therefore the circular eye mark can be arranged closer to the patient and the ophthalmology instrument can be small in size.

In any case, by using the eye mark pattern including a plurality of circular eye marks having different diameters, a patient can examine or check a degree of monocular diplopia of his or her own eye in a quantitative manner. In this case, the patient can perform the examination by oneself or a supporting person can examine a degree of monocular diplopia of the patient in a quantitative manner by hearing a reply of the patient seeing the eye mark pattern.

As explained above, in the monocular diplopia examining method according to the invention, a plurality of circular eye marks having different diameters are observed by a single eye of a patient having monocular diplopia from a predetermined examination distance to find a particular eye mark 1 under such a condition that double vision images 1' and 1" of the relevant eye mark 1 are observed to be just circumscribed each other. When such a circular eye mark 1 is found, a degree of monocular diplopia of the patient may be expressed by a diameter of this circular eye mark 1. It should be noted that a diameter of a circular eye mark is changed in accordance with the examination distance. Sometimes it is inconvenient for a user or patient. In order to remove a conception of the examination distance, a degree of monocular diplopia may be expressed by a view angle at which a patient sees a circular eye mark.

In a first embodiment according to the invention, a plurality of circular eye marks are formed by printing black circles on a background such as a white paper and diameters of these circles are successively increased. A patient observes these circular eye marks with his or her single eye to find a condition such that double vision images 1' and 1" of a particular circular eye mark 1 are observed to be just circumscribed each other, and a degree of monocular diplopia is quantitatively expressed by a view angle for this circular eye mark 1. It should be noted that since the eye mark is circular, a degree of monocular diplopia can be examined in any axial direction of monocular diplopia along which double vision images appear. As will be explained later, when the examination distance is set to five meters, a view angle of 1 minute (1/60 degrees) corresponds to a circular eye mark having a diameter of 1.45 mm.

Figure 2:
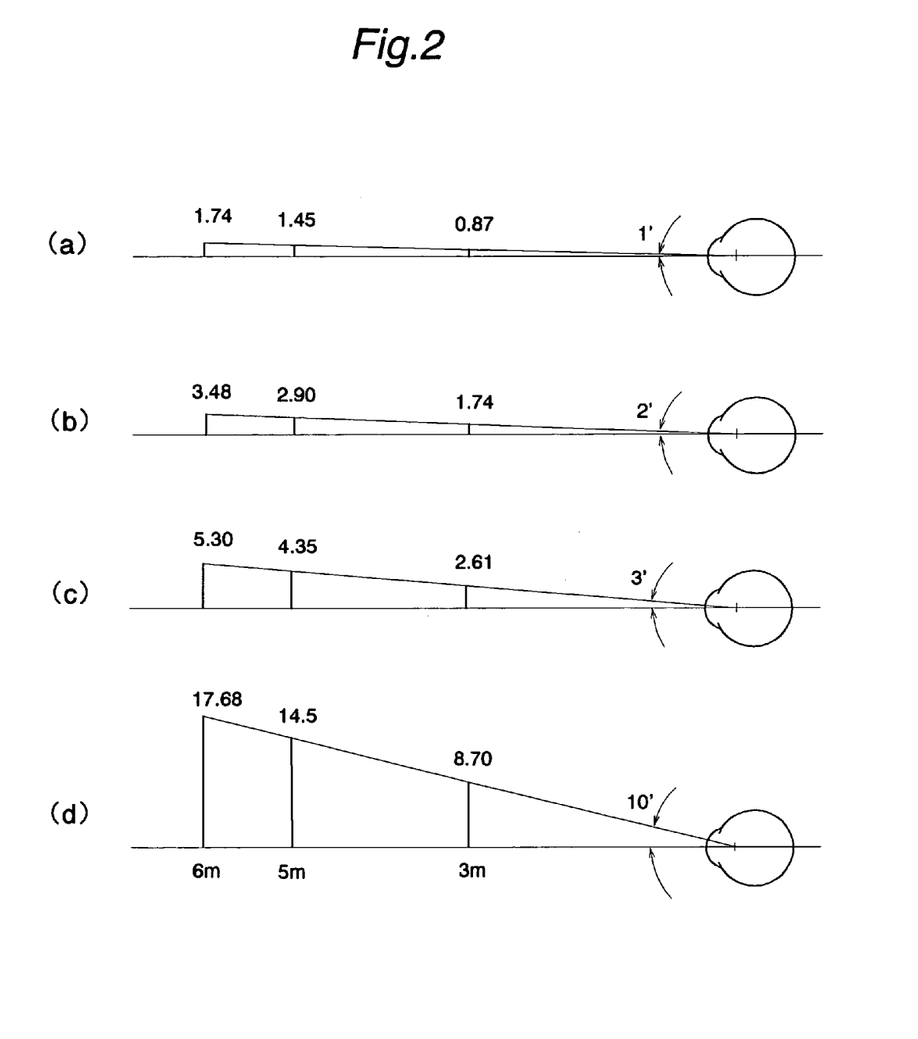

FIGS. 2(*a*)-2(*d*) are diagrams representing a geometrical relationship between a view angle, an inspection distance and a diameter of a circular eye mark. FIG. 2(*a*) shows diameters of circular eye marks for a view angle of 1 minute, FIG. 2(*b*) for 2 minutes, FIG. 2(*c*) for 3 minutes, and FIG. 2(*d*) depicts diameters of circular eye marks for 10 minutes.

A table 1 represents a relationship between view angles and diameters of circular eye marks taking the examination distances of 3 meters, 5 meters, 6 meters and 20 feet (6.069 meters) as parameters. Precisely speaking, a diameter of a circular eye mark having a view angle of 1 minute for the examination distance of 5 meters is 1.454 mm, but an approximate value of 1.45 mm is adopted in the table 1 taking into account of a possible error in forming the circular eye marks.

TABLE 1

| view angle | inspection distance | | | |
|---|---|---|---|---|
| (minute) | 3 m | 5 m | 6 m | 20 ft (6.096 m) |
| 1 | 0.87 mm | 1.45 mm | 1.74 mm | 1.77 mm |
| 2 | 1.74 | 2.9 | 3.48 | 3.54 |
| 3 | 2.61 | 4.35 | 5.22 | 5.3 |
| 4 | 3.48 | 5.8 | 6.96 | 7.07 |
| 5 | 4.35 | 7.25 | 8.7 | 8.84 |
| 6 | 5.22 | 8.7 | 10.44 | 10.6 |
| 7 | 6.09 | 10.15 | 12.18 | 12.37 |
| 8 | 6.96 | 11.6 | 13.92 | 14.14 |
| 9 | 7.83 | 13.05 | 15.66 | 15.91 |
| 10 | 8.7 | 14.5 | 17.4 | 17.68 |
| 11 | 9.57 | 15.95 | 19.14 | 19.45 |
| 12 | 10.44 | 17.4 | 20.88 | 21.21 |
| 13 | 11.31 | 18.85 | 22.62 | 22.98 |
| 14 | 12.18 | 20.3 | 24.36 | 24.75 |
| 15 | 13.05 | 21.75 | 26.1 | 26.52 |
| 16 | 13.92 | 23.2 | 27.84 | 28.28 |
| 17 | 14.79 | 24.65 | 29.58 | 30.05 |

Figure 3:
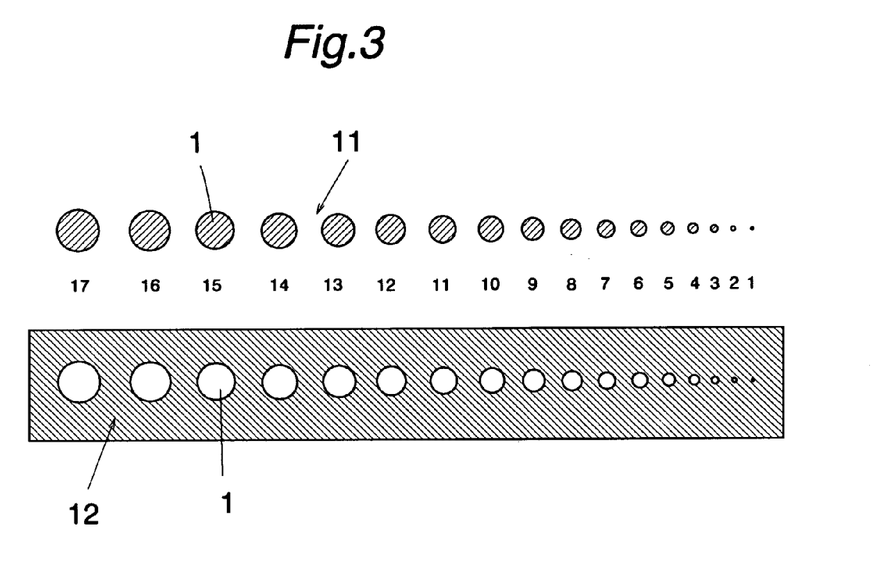
FIG. 3 is a front view showing a first embodiment of the eye mark chart according to the invention.

FIG. 3 is a front view of a second embodiment of the eye mark chart for use in the monocular diplopia examining method according to the invention. In the present embodiment, circular eye marks 1 are printed on a paper. It should be noted that the circular eye marks 1 shown to be closer to each other than an actual pattern for the sake of simplicity. As stated above, when the examination distance is set to, for instance 5 meters, a view angle of one minute corresponds to a diameter of a circular eye mark of 1.45 mm. The eye mark chart of the present embodiment includes a first array of eye marks 11 each of circular eye marks 1 being formed by black dots having different diameters expressed by view angles of 1 minute to 17 minutes and these circular eye marks 1 are arranged to form a line in order of size.

The eye mark chart further includes a second array of eye marks 12 which is formed by white circular dots having different diameters, these circular eye marks 1 are formed on a black background and are aligned to form a line in order of size just like as the first array of eye marks 11. The first and second arrays of circular eye marks 11 and 12 are arranged in parallel to each other. In the present embodiment, each of the first and second arrays of eye marks 11 and 12 includes the circular eye marks 1 having diameters corresponding to view angles from 1 minute to 17 minutes. According to the invention, an array of eye marks preferably includes at least twelve circular eye marks having diameters corresponding to view angles from 2 minutes to 13 minutes.

According to the invention, a plurality of circular eye marks 1 are arranged side by side in a horizontal direction to form a line in order of size, because when a patient observes the horizontally arranged circular eye marks 1, the patient can easily compare conditions of double vision images. Particularly, monocular diplopia caused by irregular astigmatism due to farsightedness has been most frequently observed in a daily ophthalmology examination. In this type of monocular diplopia, double vision images usually appear in an up and down direction. Therefore, the circular eye marks 1 of the eye mark chart are preferably arranged in a horizontal direction.

Upon examination, when a patient observes array of eye marks 11 or 12, each of the circular eye marks 1 is perceived as double vision images and the patient can easily find a particular eye mark whose double vision images are perceived to be circumscribed each other. Then, a degree of monocular diplopia can be determined by a view angle of the relevant eye mark 1.

When a patient has monocular diplopia as well as astigmatism due to an abnormal condition of refraction of an optical system of an eye, either one of both of the double vision images could be seen clearly. Therefore, it is preferable to prepare two kinds of circular eye marks, i.e. two kinds of stimulus. In the present embodiment, the first and second arrays of circular eye marks 11 and 12 are formed by black and white turned over patterns.

When the eye mark chart shown in FIG. 3 is used, at first a patient selects either one of the first and second arrays of eye marks 11 and 12 which can be observed much more clearly, and a degree of monocular diplopia is examined by observing the selected array of eye marks 11 or 12. If the patient might feel that the examination has not be carried out reliably, a new examination is performed using the remaining array of eye marks 12 or 11. It should be noted that in the embodiment illustrated in FIG. 3, the array of eye marks 11 formed by the black dots on the white background is provided above the second array of eye marks 12 formed by white dots on the black background. However, according to the invention, the first array of eye marks 11 may be arranged below the second array of eye marks 12.

In a modification of the second embodiment of the eye mark chart according to the invention, either one of the first and second arrays of eye marks 11 and 12 may be dispensed with. Moreover, the examination distance is not limited to 5 meters, but may be set to a different value such as 3 meter or 6 meters. In the latter cases, diameters of circular eye marks can be determined in accordance with diameter values listed in the above mentioned table 1.

Upon examination, a patient could not see the eye marks clearly from a predetermined examination distance due to a strong deficiency of refraction or cataract, the patient may move closer to or far from the eye mark chart. In this case, a detected view angle can be corrected in accordance with a distance over which the patient moved closer to or far away from the eye mark chart.

Figure 4:
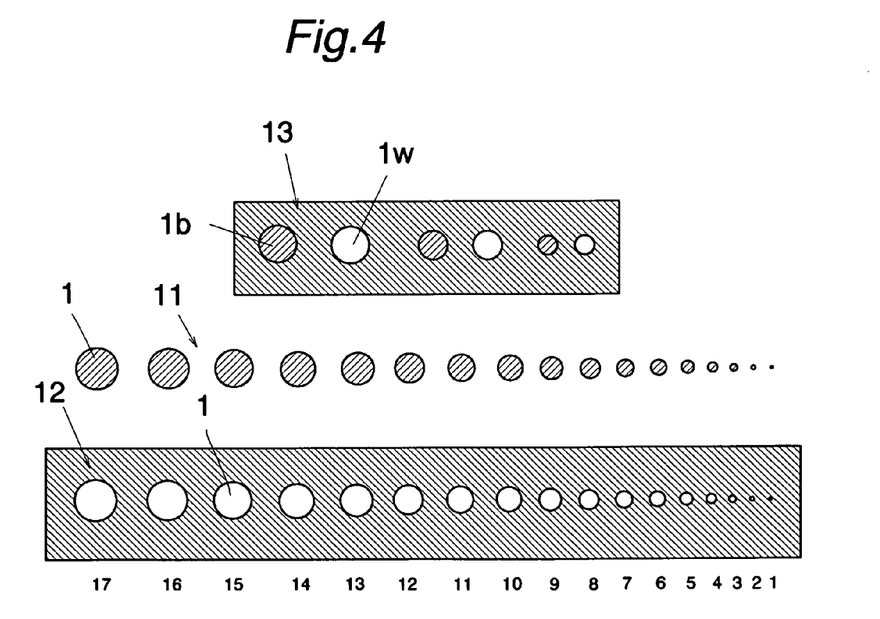
FIG. 4 is a front view depicting a second embodiment of the eye mark chart according to the invention.

FIG. 4 is a front view showing a third embodiment of the eye mark chart according to the invention. The eye mark chart includes a third array of eye marks 13 in addition to the first and second arrays of eye marks 11 and 12 shown in FIG. 3. The third array of eye marks 13 is composed of several pairs of black and white circular eye marks 1b and 1w described on a red background. Diameters of black and white eye marks belonging to the same pair are identical with each other, but diameters of black and white eye marks belonging to different pairs differ from each other.

The third array of eye marks 13 is utilized to check weather or not double vision images have different foci or aberrations. When double vision images of a black circular eye mark 1b and double vision images of a white eye mark 1w are compared with each other, if a degree of monocular diplopia for the black eye mark on the red background is larger than that for the white eye mark on the red background, it is presumed that an aberration of the double vision images of the black eye mark is much larger and a condition of monocular diplopia of a patient may be diagnosed to be much sever.

As explained above, when a difference in aberration of foci of double vision images can be examined by means of the third array of eye marks 13, it may presume which one of double vision images reveals a true focus or a focus much closer to the true focus.

Figure 5:
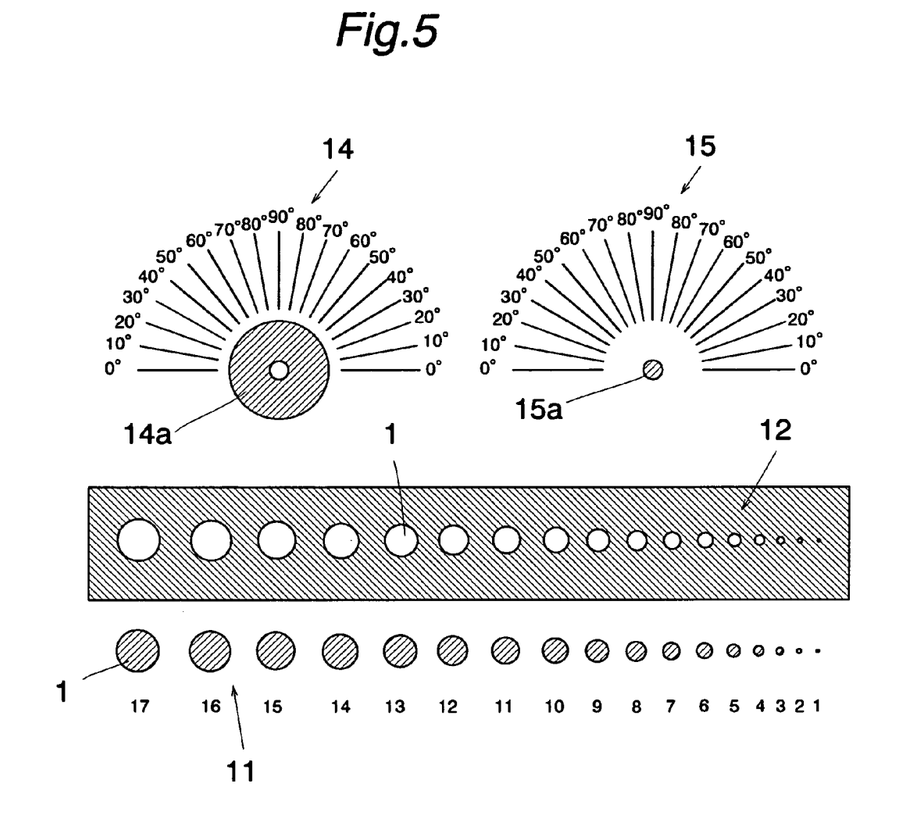
FIG. 5 is a front view illustrating a third embodiment of the eye mark chart according to the invention.

FIG. 5 is a front view illustrating a fourth embodiment of the eye mark chart according to the invention. The eye mark chart of the present embodiment includes first and second semicircular eye marks for astigmatism inspection 14 and 15 in addition to the first and second arrays of eye marks 11 and 12. At a center of the first semicircular eye mark for astigmatism inspection 14, there is provided a white circular eye mark 14a on a black background, and at a center of the second semicircular eye mark for astigmatism inspection there is arranged a black circular eye mark 15a on a white background. Each of the first and second semicircular eye marks for astigmatism inspection 14 and 15 is formed by a number of radial lines.

A degree of monocular diplopia can be examined using either or both of the first and second arrays of eye marks 11 and 12, and an axial direction along which double vision image appear can be judged using the first and second semicircular eye marks for astigmatism inspection 14 and 15.

Figure 6:
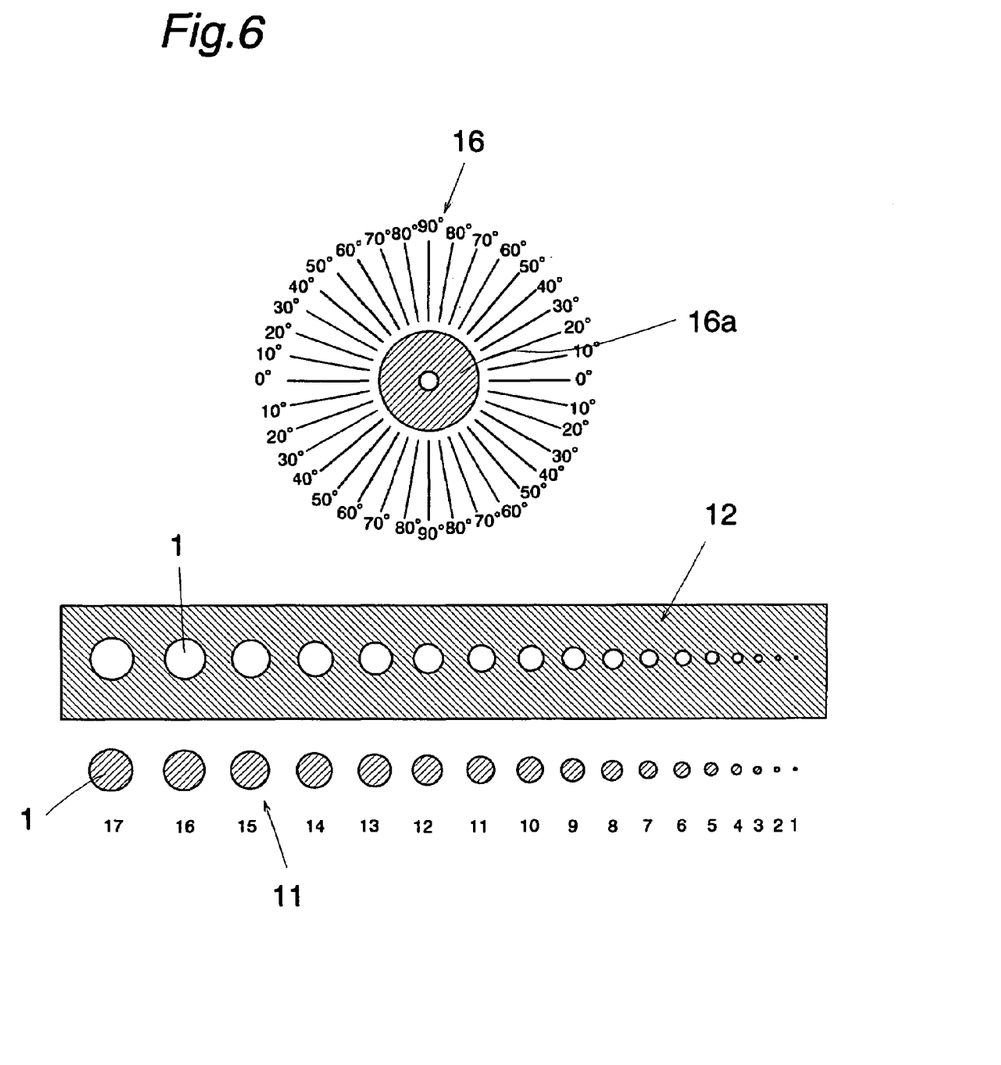
FIG. 6 is a front view showing a fourth embodiment of the eye mark chart according to the invention.

FIG. 6 is a front view depicting a fifth embodiment of the eye mark chart according to the invention. In this embodiment, a circular eye mark for astigmatism inspection is arranged above the first and second arrays of eye marks 11 and 12. At a center of the circular eye mark for astigmatism inspection 16 there is provided a white circular eye mark 16a on a black background. The circular eye mark for astigmatism inspection 16 is formed by a number of radial lines extending to a center of the circular white eye mark 16a. Since the radial lines are formed around all periphery of the circular eye mark 16a, an axial direction of astigmatism can be inspected much more precisely.

Figure 7:
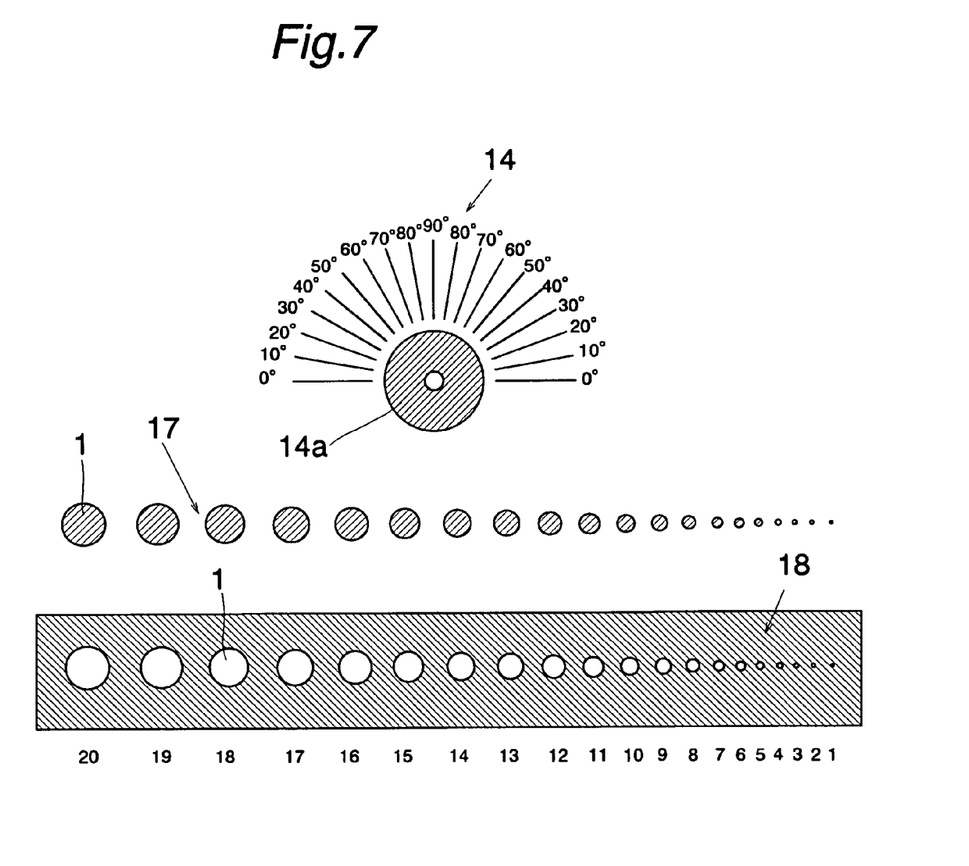
FIG. 7 is a front view representing a fifth embodiment of the eye mark chart according to the invention.

FIG. 7 is a front view showing a sixth embodiment of the eye mark chart according to the invention. In the present embodiment a first array of circular eye marks for monocular diplopia inspection 17 is formed by twenty black dots 1 on a white background and a second array of circular eye marks for monocular diplopia 18 is formed by twenty white dots 1 on a black background. Since the number of the eye marks 1 of the first and second arrays 17 and 18 is twenty, a range of a degree of monocular diplopia can be extended. The eye mark chart further comprises a semicircular eye mark for astigmatism inspection 14 having a white circular eye mark 14a for astigmatism inspection formed on a black background. Even by utilizing the eye mark chart composed of a simple combination of eye marks, a degree of monocular diplopia can be examined easily.

The invention claimed is:

1. A method of examining a degree of monocular diplopia of a patient, wherein a plurality of circular eye marks having different diameters are seen by a single eye of the patient to find a particular circular eye mark whose double vision images are observed to be circumscribed each other, and a degree of monocular diplopia of the patient is examined on a basis of a view angle of said particular circular eye mark.

2. The method according to claim 1, wherein said plurality of circular eye marks are formed on an eye mark chart and the eye mark chart is observed by the patient from a predetermined examination distance.

3. The method according to claim 2, wherein said eye mark chart is observed by the patient from a distance which is shorter or longer than said predetermined examination distance and the examined degree of monocular diplopia is corrected in accordance with a difference between the predetermined examination distance and the actually examined distance.

4. The method according to claim 1 wherein said plurality of circular eye marks are displayed on a monitor screen of an ophthalmology instrument including an eye lens, said monitor screen being placed at a conjugate position of the eye of the patient with respect to the eye lens, and images of the circular eye marks displayed on the monitor screen are observed through the eye lens.

5. The method according to claim 4, wherein said images of circular eye marks are successively displayed on the monitor screen one by one.

6. The method according to claim 4, wherein a plurality of said images of eye marks are simultaneously displayed on the monitor screen.

7. An eye mark chart for use in a method of examining a degree of monocular diplopia in a quantitative manner in which a plurality of circular eye marks having different diameters are observed with a single eye a patient to find a particular circular eye mark whose diplopia vision images are observed to be circumscribed each other and a degree of monocular diplopia is determined as a view angle of the relevant particular eye mark, comprising an arrangement of a plurality of circular eye marks having different diameters, said circular eye marks forming a line in order of size.

8. The eye mark chart according to claim 7, wherein each of said circular eye marks is formed by a circular black line described on a white background.

9. The eye mark chart according to claim 7, wherein each of said circular eye marks is formed by a black dot described on a white background.

10. The eye mark chart according to claim 7, wherein each of said circular eye marks is formed by a circular white line described on a black background.

11. The eye mark chart according to claim 7, wherein each of said circular eye marks is formed by a white dot described on a black background.

12. The eye mark chart according to claim 8, wherein said circular eye marks are arranged horizontally to form a line in order of size.

13. The eye mark chart according to claim 7, comprising a first array of circular eye marks arranged horizontally to form a line in order of size, each of said circular eye marks of the first array being formed by a white dot described on a black background and a second array of circular eye marks arranged horizontally to form a line in order of size, each of said circular eye marks of the second array being formed by a black dot described on a white background, and said first and second arrays of circular eye marks are arranged one above the other.

14. The eye mark chart according to claim 13, further comprising a third array of plural pairs of circular eye marks arranged horizontally, each pair includes black and white dots of a same diameter described on red background and diameters of the black and white dots belonging to different pairs differ from each other.

15. The eye mark chart according to claim 13, further comprising at least circular or semicircular eye marks for astigmatism inspection formed by radial lines.

16. The eye mark chart according to claim 9, wherein said circular eye marks are arranged horizontally to form a line in order of size.

17. The eye mark chart according to claim 10, wherein said circular eye marks are arranged horizontally to form a line in order of size.

* * * * *